(12) United States Patent
Drahm et al.

(10) Patent No.: US 6,840,109 B2
(45) Date of Patent: Jan. 11, 2005

(54) VIBRATORY TRANSDUCER

(75) Inventors: Wolfgang Drahm, Erding (DE); Alfred Rieder, Landshut (DE)

(73) Assignee: Endress + Hauser Flowtec AG (CH)

(*) Notice: Subject to any disclaimer, the term of this patent is extended or adjusted under 35 U.S.C. 154(b) by 86 days.

(21) Appl. No.: 10/431,640

(22) Filed: May 8, 2003

(65) Prior Publication Data

US 2003/0233878 A1 Dec. 25, 2003

Related U.S. Application Data

(60) Provisional application No. 60/393,116, filed on Jul. 3, 2002, and provisional application No. 60/400,047, filed on Aug. 2, 2002.

(30) Foreign Application Priority Data

May 8, 2002 (DE) ......................................... 102 20 827
Aug. 1, 2002 (DE) ......................................... 102 35 322

(51) Int. Cl.$^7$ ................................................. G01F 1/84
(52) U.S. Cl. .................... 73/650; 73/861.357; 73/54.41
(58) Field of Search ....................... 73/650, 592, 54.41, 73/861.351–861.357, 32 A

(56) References Cited

U.S. PATENT DOCUMENTS

| | | | |
|---|---|---|---|
| 4,524,610 A | 6/1985 | Fitzgerald et al. | .......... 73/32 A |
| 5,253,533 A | 10/1993 | Lam et al. | ............ 73/861.357 |
| 5,531,126 A | 7/1996 | Drahm | .................. 73/861.357 |
| 5,969,265 A | 10/1999 | VanCleve et al. | ...... 73/861.357 |
| 6,006,609 A | 12/1999 | Drahm et al. | .......... 73/861.357 |
| 6,041,665 A | 3/2000 | Hussain | ................. 73/861.357 |
| 6,374,478 B1 | 4/2002 | Neece et al. | .................... 29/595 |
| 6,397,685 B1 | 6/2002 | Cook et al. | ............ 73/861.357 |
| 6,477,902 B1 * | 11/2002 | Oosawa et al. | ........ 73/861.355 |
| 6,516,674 B1 * | 2/2003 | Poremba | ................. 73/861.357 |
| 6,666,098 B2 * | 12/2003 | Drahm et al. | .......... 73/861.355 |
| 2002/0117010 A1 * | 8/2002 | Drahm et al. | .......... 73/861.357 |

FOREIGN PATENT DOCUMENTS

| | | |
|---|---|---|
| DE | 100 20 606 A1 | 10/2001 |
| EP | 0 849 568 A1 | 6/1998 |
| EP | 1 253 408 A1 | 10/2002 |
| JP | 10-221146 | 8/1998 |
| JP | 2000-55710 | 2/2000 |
| WO | WO 95/16897 | 6/1995 |
| WO | WO 00/14485 | 3/2000 |

* cited by examiner

*Primary Examiner*—Hezron Williams
*Assistant Examiner*—Rose M. Miller
(74) *Attorney, Agent, or Firm*—Bacon & Thomas, PLLC

(57) ABSTRACT

To conduct a fluid, the transducer has a flow tube which in operation vibrated by an excitation assembly. Inlet-side and outlet-side vibrations of the flow tube are sensed by means of a sensor arrangement. To produce shear forces in the fluid, the flow tube is at least intermittently excited into torsional vibrations about a longitudinal flow-tube axis. An internal portion of the transducer, formed at least by the flow tube, an antivibrator, the sensor arrangement, and the excitation assembly and mounted at least on the inlet and outlet tube sections, has a centroid which is located inside the flow tube. The transducer is suitable for use in viscometers or Coriolis mass flowmeter-viscometers. In spite of using only a single straight flow tube, it is dynamically well balanced in operation, and the development of bending moments by the torsionally vibrating flow tube is largely prevented. This also effectively prevents the transducer case or the connected pipe from being excited into sympathetic vibration. Measurement signals representative of mass flow rate are readily distinguishable from measurement signals representative of viscosity, particularly if the sensors used for the viscosity measurement are also used for the mass flow measurement.

15 Claims, 4 Drawing Sheets

VIBRATORY TRANSDUCER

This application claims the benefit under 35 USC 119 of the following prior filed provisional applications: 60/393,116, filed Jul. 3, 2002; and 60/400,047, filed Aug. 2, 2002.

FIELD OF THE INVENTION

This invention relates to a vibratory transducer which is particularly suited for use in a viscometer, a viscometer-densimeter, or a viscometer-mass flowmeter.

BACKGROUND OF THE INVENTION

To determine the viscosity of a liquid flowing in a pipe, use is frequently made of meters which, using a vibratory transducer, comprising a flow tube communicating with the pipe, and control and evaluation electronics connected thereto, induce shear or friction forces in the fluid and derive therefrom a measurement signal representing the viscosity.

U.S. Pat. Nos. 4,524,610, 5,253,533, 6,006,609, or EP-A 1 158 289, for example, disclose in-line viscometers, i.e., viscometers connectable into a fluid-conducting pipe, with a vibratory transducer which responds to the viscosity of the fluid flowing in the pipe and comprises: a single straight flow tube for conducting the fluid which vibrates in operation and communicates with the pipe via an inlet tube section and an outlet tube section; an excitation assembly which in operation excites at least part of the flow tube into torsional vibrations about an axis of vibration aligned with the flow tube; and a sensor arrangement for locally sensing vibrations of the flow tube.

As is well known, straight flow tubes, when excited into torsional vibrations about an axis aligned with the flow tube, cause shear forces to be produced in the fluid flowing through the tube, whereby vibrational energy is removed from the torsional vibrations and dissipated in the fluid. This results in the torsional vibrations of the flow tube being damped, so that additional excitation energy must be supplied to the flow tube to maintain those vibrations.

In operation, the flow tubes of such transducers used in in-line viscometers, for example, are generally excited at an instantaneous resonance frequency of a torsional fundamental mode, particularly with the vibration amplitude maintained at a constant value. It is also common practice to excite the flow tubes for viscosity measurements, simultaneously or alternately with the torsional mode, into flexural vibrations, usually also at a resonance frequency of a flexural fundamental mode, see also the above referred to U.S. Pat. No. 4,524,610. Since this flexural resonance frequency is also dependent on the instantaneous density of the fluid in particular, such meters can also be used to measure the density of fluids flowing in pipes. Furthermore, Coriolis forces dependent on the instantaneous mass flow rate are induced in the fluid flowing through such flow tubes vibrating in a flexural mode, so that such transducers are also suitable for measuring the mass flow rate of the fluid, see also U.S. Pat. No. 6,006,609 or EP-A 1 158 289.

Compared with the use of bent flow tubes for viscosity measurements, the use of straight flow tubes vibrating in the manner described above, as is well known, has the advantage that shear forces are induced in the fluid over virtually the entire length of the flow tube, particularly with a great depth of penetration in the radial direction, so that very high sensitivity of the transducer to the viscosity to be measured can be achieved. Another advantage of straight flow tubes is that they can be drained residue-free with a high degree of reliability in virtually any position of installation, particularly after a cleaning operation performed in-line. Furthermore, such flow tubes are much simpler and, consequently, less expensive to manufacture than, for example, an omega-shaped or helically bent flow tube.

An essential disadvantage of the above-described transducers lies in the fact that in operation, torsional vibrations can be transmitted from the transducer via the flow tube and any transducer case that may be present to the connected pipe. This, in turn, may result in a zero shift, and hence in measurement inaccuracies. Furthermore, the loss of vibrational energy to the transducer's environment may result in a substantial deterioration of efficiency and possibly also in a degradation of the signal-to-noise ratio in the measurement signal.

SUMMARY OF THE INVENTION

It is therefore an object of the invention to provide a vibratory transducer which is particularly suited for a viscometer or a Coriolis mass flowmeter-viscometer and which, while using only a single straight flow tube, is dynamically well balanced in operation, and in which the development of bending moments by the torsionally vibrating flow tube is made virtually impossible, so that any excitation of the transducer case or of the connected pipe into sympathetic vibrations is effectively prevented. In addition, measurement signals representative of mass flow rate are to be optimally distinguishable from the measurement signals representative of viscosity, particularly if the sensors used for the viscosity measurement are also used for the mass flow measurement.

To attain the object, the invention provides a vibratory transducer for a fluid flowing in a pipe. The transducer comprises an essentially straight flow tube of predeterminable diameter for conducting the fluid which communicates with the connected pipe via an inlet tube section, ending in an inlet-side end of the flow tube, and an outlet tube section, ending in an outlet-side end of the flow tube. In operation, the flow tube is at least intermittently vibrated, such that, particularly in order to produce shear forces in the fluid, at least a portion of the flow tube performs torsional vibrations about an axis of torsional vibration essentially aligned with the inlet tube section and the outlet tube section, said torsional vibrations having a predeterminable frequency. Furthermore, the transducer comprises an antivibrator having a predeterminable torsional natural frequency, said antivibrator being fixed at the inlet-side and outlet-side ends of the flow tube. The transducer further comprises an excitation assembly acting on the flow tube and the antivibrator for vibrating at least the flow tube, and a sensor arrangement for sensing vibrations of the flow tube. An internal portion of the transducer, formed at least by the flow tube, the antivibrator, the sensor arrangement, and the excitation assembly and mounted at least on the inlet and outlet tube sections, has a centroid which is located inside the flow tube.

In a first embodiment of the invention, the centroid of the internal portion is located as precisely as possible on a longitudinal flow-tube axis, particularly on an axis aligned with the inlet tube section and the outlet tube section.

In a second embodiment of the invention, the internal portion has a first principal axis of inertia which is essentially aligned with the inlet tube section and the outlet tube section and lies within the flow tube.

In a third embodiment of the invention, the internal portion has an essentially symmetric mass distribution with respect to the axis of torsional vibration.

In a fourth embodiment of the invention, the antivibrator is essentially tubular in shape and essentially coaxial with the flow tube.

In a fifth embodiment of the invention, a frequency of torsional vibrations of the flow tube and a torsional natural frequency of the antivibrator are at least approximately equal.

In a sixth embodiment of the invention, a torsional natural frequency of the antivibrator is greater than 0.8 times a torsional natural frequency of the flow tube.

In a seventh embodiment of the invention, the torsional natural frequency of the antivibrator is less than 1.2 times a torsional natural frequency of the flow tube.

According to a development of the invention, the flow tube at least intermittently performs flexural vibrations about its longitudinal axis, particularly in order to induce Coriolis forces in the fluid.

In an eighth embodiment of the invention, a torsional vibration frequency and a flexural vibration frequency of the flow tube are chosen to be different.

In a ninth embodiment of the invention, the excitation assembly is so designed and so fixed to the flow tube and the antivibrator that a force generating the flexural vibrations will act on the flow tube along an imaginary line of force which runs outside a second principal axis of inertia, an axis perpendicular to the first principal axis of inertia, or intersects the second principal axis of inertia at one point at the most.

In a tenth embodiment of the invention, the excitation assembly comprises an excitation coil which is fixed to the flow tube, is at least intermittently traversed by an excitation current during operation, and acts on the flow tube and the antivibrator via a lever connected with the antivibrator and via an armature fixed in the lever.

In an eleventh embodiment of the invention, the sensor arrangement comprises a sensor coil disposed in the transducer outside the second principal axis of inertia as well as an armature magnetically coupled thereto whose relative position, particularly whose spacing, is changed as a result of the torsional and, if excited, flexural vibrations of the flow tube and the antivibrator, whereby a variable measurement voltage is at least intermittently induced in the sensor coil.

In a twelfth embodiment of the invention, the transducer comprises a transducer case fixed to the flow tube on the inlet and outlet sides.

In a thirteenth embodiment of the invention, additional masses are fixed to the flow tube and/or grooves are formed in the antivibrator to adjust the mass distribution of the internal portion.

One basic idea of the invention is to dynamically balance the transducer by arranging that reactive torques at least approximately equal to the torques developed by the torsionally vibrating flow tube are developed by the antivibrator. On the other hand, insofar as possible, no bending moments are to be produced, for instance as a result of increased pendular motions if the centroid is located outside the flow tube.

Another basic idea of the invention is to design the excitation assembly or the sensor arrangement in such a way that both the torsional vibrations and the flexural vibrations of the flow tube can be generated by means of the same excitation assembly and sensed by means of the same sensor coils, particularly simultaneously, and that, on the other hand, the generated and sensed torsional or flexural vibration can be readily separated from each other in the measurement signal.

One advantage of the invention lies in the fact that the transducer, despite possible operational variations in the density and/or viscosity of the fluid, is balanced in a simple and robust manner such that internal torques can be largely kept away from the connected pipe. In addition, the transducer can also be dynamically balanced for flexural vibrations, at least for a small density range. Another advantage is that as a result of this constructionally very simple vibration isolation, the transducer according to the invention can be made very compact and very light.

A further advantage of the invention is that, at least if the torsional frequency and the flexural vibration frequency of the flow tube are chosen to be different, the various quantities to be measured, particularly mass flow rate, viscosity, or density, can be measured even if torsional and flexural vibrations are excited simultaneously.

BRIEF DESCRIPTION OF THE DRAWINGS

The invention and further advantages will become more apparent by reference to the following description of an embodiment when taken in conjunction with the accompanying drawings. Like reference characters have been used to designate like parts throughout the various figures; reference characters that were already assigned have been omitted in subsequent figures if this contributes to clarity. In the drawings.

DETAILED DESCRIPTION OF EXEMPLARY EMBODIMENTS

Figure 1:
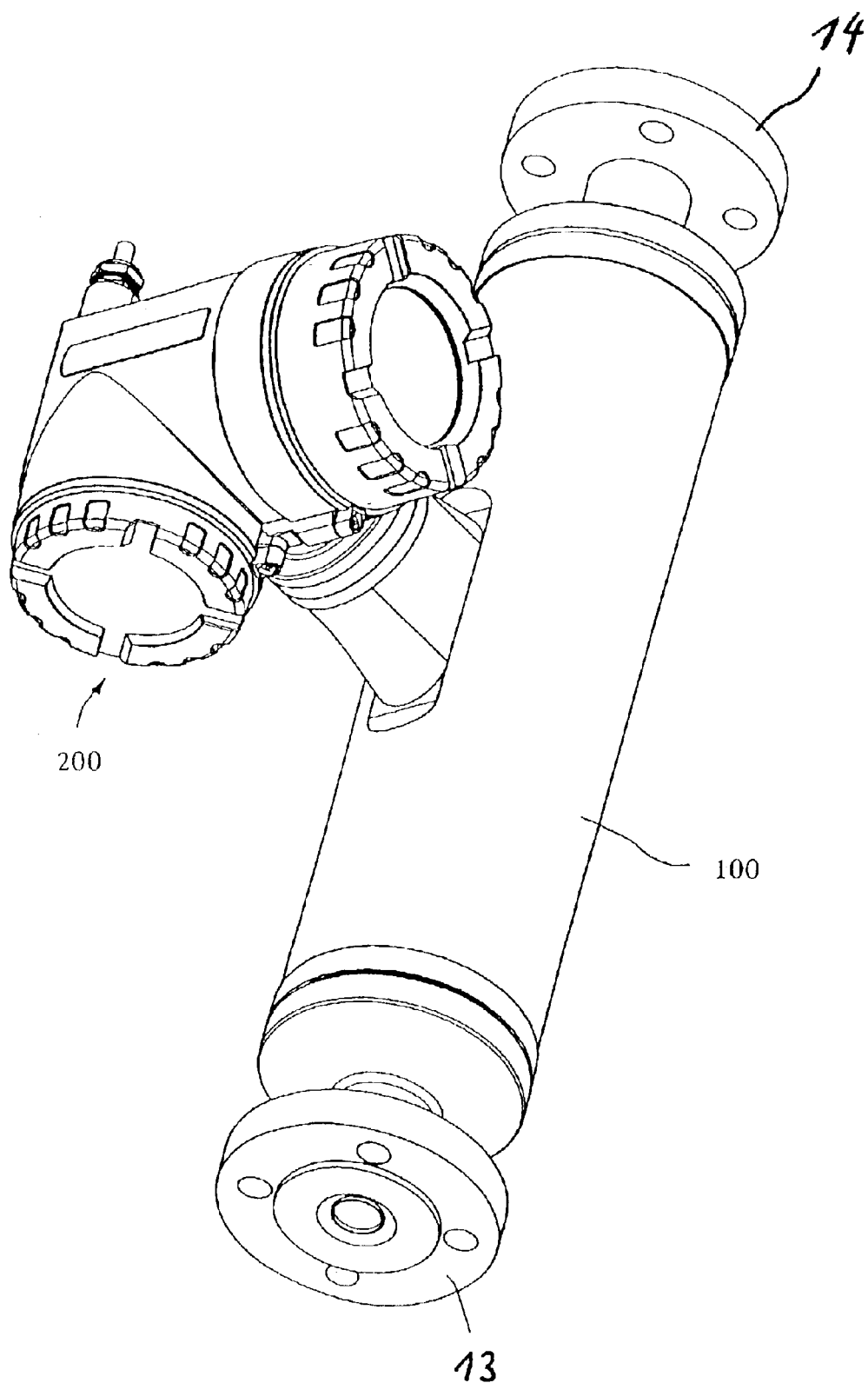
FIG. 1 shows a meter designed to be connected into a pipe for measuring the viscosity of a fluid flowing in the pipe.

While the invention is susceptible to various modifications and alternative forms, exemplary embodiments thereof have been shown by way of example in the drawings and will herein be described in detail. It should be understood, however, that there is no intent to limit the invention to the the particular forms disclosed, but on the contrary, the intention is to cover all modifications, equivalents, and alternatives falling within the spirit and scope of the invention as defined by the intended claims.

Referring now to FIG. 1, there is shown a meter designed to be connected into a pipe (not shown) for measuring the viscosity of a fluid flowing in the pipe. In addition, the meter may also serve to measure the mass flow rate and/or the density of the fluid. Therefor, meter comprises a vibratory transducer through which the fluid to be measured flows in operation. FIGS. 2 to 6 show schematically embodiments and developments of such a vibratory transducer.

The vibratory transducer serves to generate in a fluid flowing therethrough mechanical reaction forces, particularly viscosity-dependent friction forces, which react on the transducer and are measurable, particularly using sensor technology. From these reaction forces, a viscosity $\eta$ of the fluid, for example, can be derived in the manner familiar to those skilled in the art.

To conduct the fluid, the transducer comprises an essentially straight flow tube 10 of predeterminable diameter, particularly a single tube, which in operation is at least intermittently vibrated and thus repeatedly elastically deformed.

To permit flow of fluid through flow tube 10, the latter is connected to a fluid-conducting pipe (not shown) via an inlet tube section 11, ending in an inlet-side end 11# of flow tube 10, and an outlet tube section 12, ending in an outlet-side end 12# of flow tube 10. Flow tube 10, inlet tube section 11, and outlet tube section 12 are, insofar as possible, aligned with each other and with an imaginary longitudinal axis L. Advantageously, they are integrally formed, so that a single tubular semifinished product, for example, can be used for their manufacture; if necessary, however, flow tube 10 and tube sections 11, 12 can also be made from separate semifinished products that are subsequently joined together, for instance welded together. For flow tube 10, virtually any of the materials commonly used for such transducers, e.g., steel, titanium, zirconium, etc., may be used.

If the transducer is to be nonpermanently connected with the pipe, a first flange 13 and a second flange 14 are formed on inlet tube section 11 and outlet tube section 12, respectively; if necessary, however, inlet and outlet tube sections 11, 12 may also be connected with the pipe directly, for instance by welding or brazing. Furthermore, as shown schematically in FIG. 1, a transducer case 100 housing the flow tube 10 is fixed to inlet and outlet tube sections 11, 12, see FIGS. 1 and 2.

Straight flow tubes, when excited into torsional vibrations about an axis of torsional vibration, may cause shear forces to be produced in the fluid flowing through the tube, whereby vibrational energy is removed from the torsional vibrations, which dissipates to the fluid. As a result, the torsional vibrations of the flow tube are damped, so that additional excitation energy must be supplied to the flow tube to maintain those vibrations. Accordingly, to produce friction forces in the fluid which correspond to the viscosity of the fluid, in operation, flow tube 10 is at least intermittently excited into torsional vibrations about an axis of torsional vibration, particularly in the range of a torsional natural frequency, such that it is twisted essentially according to a torsional natural vibration mode shape about its longitudinal axis L or an axis substantially parallel thereto, see also, for instance, U.S. Pat. Nos. 4,524,610, 5,253,533, 6,006,609, or EP-A 1 158 289.

The flow tube 10 may be excited at a torsional frequency corresponding as exactly as possible to a natural resonance frequency of that fundamental torsional eigenmode in which flow tube 10 is twisted essentially unidirectionally over its entire length. In the case of a flow tube 10 of special steel with a nominal diameter of 20 mm, a wall thickness of about 1.2 mm, and a length of about 350 mm and with attachments (see below), a natural resonance frequency of this fundamental torsional eigenmode may be, for instance, of the order of about 1500 to 2000 Hz.

According to a development of the invention, during operation of the transducer, flow tube 10, in addition to being excited into torsional vibrations, is excited, particularly simultaneously therewith, into flexural vibrations in such a way as to be deflected essentially according to a natural first flexural vibration mode shape. The flow tube 10 may be excited at a flexural vibration frequency corresponding as exactly as possible to a lowest natural flexural resonance frequency of flow tube 10, so that the vibrating, but empty flow tube 10 is deflected essentially symmetrically with respect to a central axis perpendicular to the longitudinal axis and has a single antinode. In the case of a flow tube 10 of special steel with a nominal diameter of 20 mm, a wall thickness of about 1.2 mm, and a length of about 350 mm as well as with the usual attachments, this lowest flexural resonance frequency may be of the order of about 850 to 900 Hz.

When a fluid flows through the pipe, so that the mass flow rate m is nonzero, Coriolis forces are induced in the fluid by flow tube 10 vibrating in a flexural mode. The Coriolis forces react on flow tube 10, thus causing an additional deformation (not shown) of flow tube 10 according to a natural second flexural vibration mode shape, which is coplanar with the first flexural vibration mode shape. The instantaneous shape of the deformation of flow tube 10, particularly in regard to its amplitudes, is also dependent on the instantaneous flow rate m. The second flexural vibration mode shape, the so-called Coriolis mode, may be, for instance, an antisymmetric flexural vibration mode shape with two or four antinodes, as is usual with such transducers.

As mentioned above, on the one hand, the torsional vibrations are damped by a desired energy loss to the fluid, which is sensed, particularly for the purpose of measuring viscosity. On the other hand, however, vibrational energy may also be removed from the vibrating flow tube 10 if components mechanically coupled to the flow tube, such as case 100 or the connected pipe, are also excited into vibration. While the energy loss to case 100, even though undesired, could still be calibrated, at least the energy loss to the transducer's environment, particularly to the pipe, occurs in a practically nonreproducible or even unpredeterminable manner.

To suppress such a loss of torsional vibrational energy to the environment, the transducer incorporates an antivibrator 20 fixed to flow tube 10 at the inlet-side and outlet-side ends thereof.

Antivibrator 20 serves to develop reactive torques which largely balance torques developed by the single flow tube 10 being twisted about its longitudinal axis L, thus keeping the transducer's environment, particularly the connected pipe, substantially free from dynamic torques. For the above-described case where flow tube 10 is additionally excited into flexural vibrations, antivibrator 20 also serves to dynamically balance the transducer for a predetermined fluid density value, e.g., a value most frequently to be expected during operation of the transducer or a critical value, to the point that any transverse forces and/or bending moments that may be produced in the vibrating flow tube 10 are largely balanced, see also applicant's European Patent Application 01 109 977.7, which was not published prior to the filing date of the present application.

For these purposes, in operation, antivibrator 20, which may be torsionally elastic and/or flexible like flow tube 10, is torsionally vibrated out of phase with, particularly in phase opposition to, flow tube 10. Accordingly, at least one of the torsional natural frequencies of antivibrator 20 is tuned as precisely as possible to the torsional frequency of the flow tube at which the latter is vibrated in operation. At any rate, however, flow tube 10 and antivibrator 20 are so adapted to one another, and antivibrator 20 is so fixed to flow tube 10, that even with flow tube 10 torsionally vibrating and antivibrator 20 covibrating, inlet tube section 11 and outlet tube section 12 are kept substantially free of torsional stress; if necessary, the flexural natural frequency of antivibrator 20 is also tuned as precisely as possible to the flexural vibration frequency of the flow tube, and during operation of the transducer, antivibrator 20 is also excited into flexural vibrations which are essentially coplanar with any flexural vibrations of flow tube 10.

Figure 2:
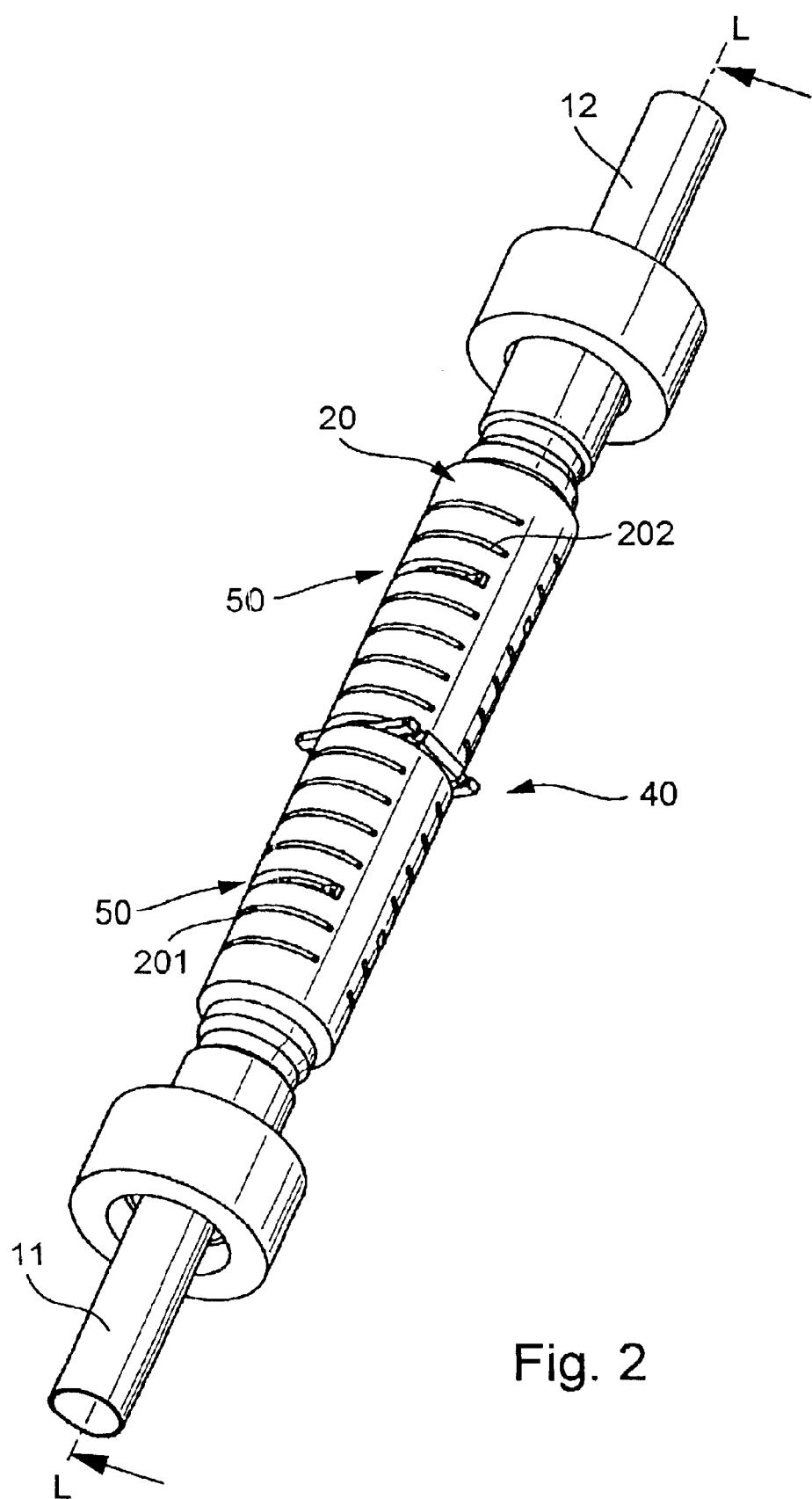
FIG. 2 is a perspective view of one embodiment of a vibratory transducer suitable for use in the meter of FIG. 1.

Antivibrator 20 may be integrally formed, as shown schematically in FIG. 2. If necessary, antivibrator 20 may also be of multipart construction as shown in U.S. Pat. No. 5,969,265, EP-A 317 340, or WO-A 00/14485, for example, or be implemented with two separate antivibrators fixed to flow tube 10 at the inlet-side and outlet-side ends of flow tube 10, see FIG. 6.

Figure 3:
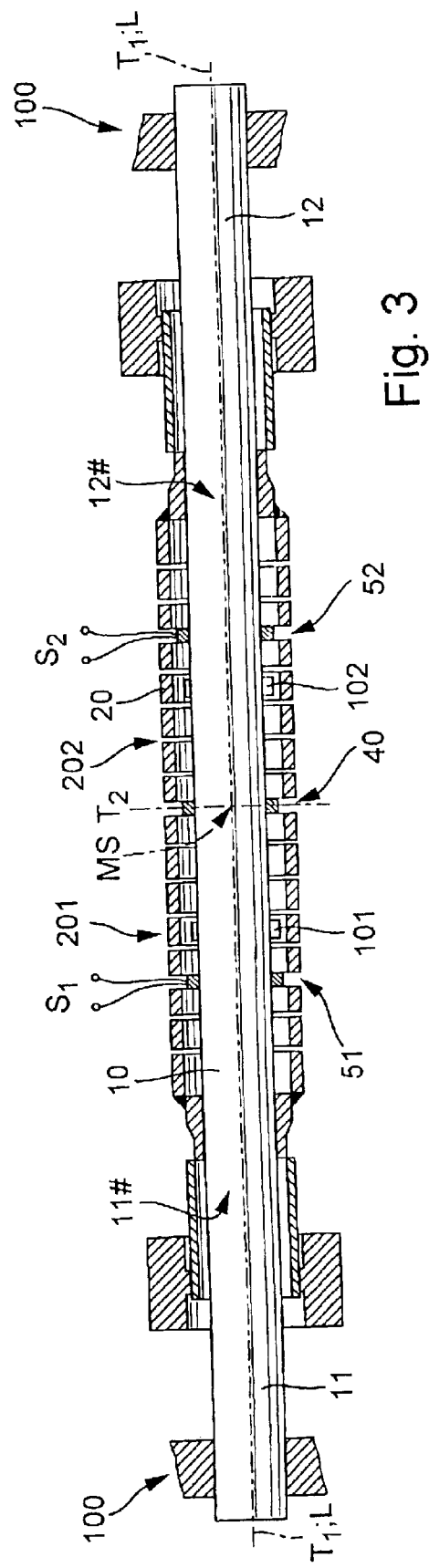
FIG. 3 is a sectional side view of the transducer of FIG. 2.
Figure 6:
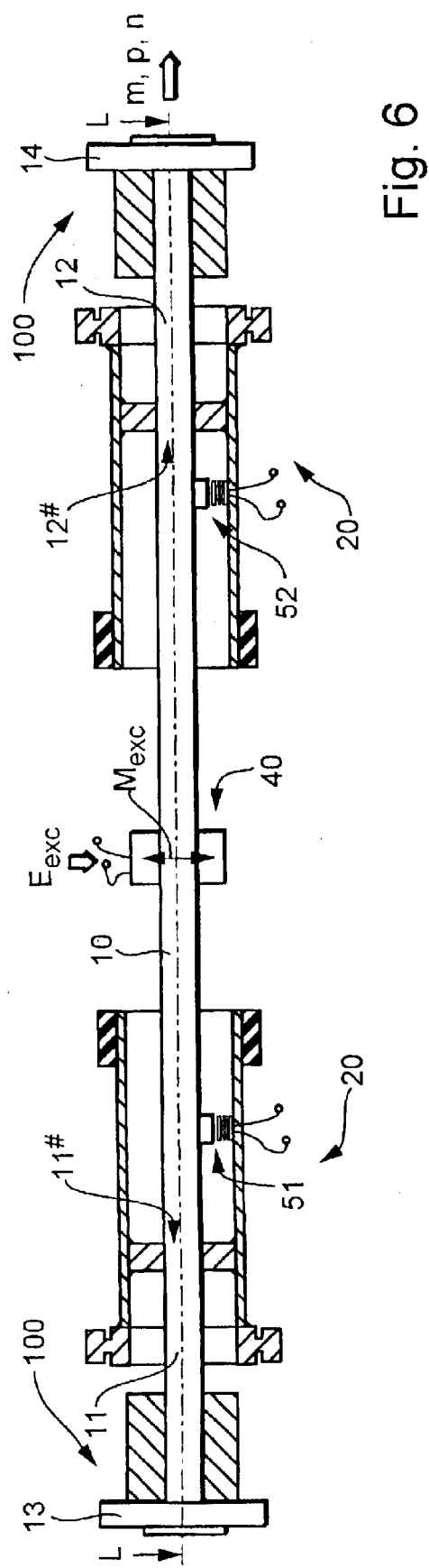
FIG. 6 is a sectional side view of another embodiment of a vibratory transducer suitable for use in the meter of FIG. 1.

As shown schematically in FIGS. 2, 3, or 6, in order to improve the measurement accuracy of the transducer or reduce its susceptibility to interference, the respective lengths of flow tube 10, antivibrator 20, and inlet and outlet tube sections 11, 12 may be so adapted to one another that in operation, inlet and outlet tube sections 11, 12 are also elastically deformed and thus can absorb part of the vibrational energy that may be lost by the internal portion of the transducer. The respective spring constants of inlet and outlet tube sections 11, 12 are so adapted to the total mass of an internal portion formed by flow tube 10 and the attachments fixed thereto, such as excitation assembly 40, sensor arrangement 50, and possibly antivibrator 20, that a lowest resonance frequency, particularly a lowest torsional resonance frequency, of the vibrating system thus formed is lower than the torsional frequency at which flow tube 10 is at least predominantly vibrated in operation.

To generate mechanical vibrations of flow tube 10, particularly the aforementioned torsional and/or flexural vibrations, the transducer further comprises an excitation assembly 40, particularly an electrodynamic exciter. Excitation assembly 40 serves to convert electric excitation energy $E_{exc}$ supplied from control electronics (not shown), for instance with a regulated current and/or a regulated voltage, into an excitation moment $M_{exc}$ which acts on flow tube 10, for instance in a pulsed manner or harmonically, and elastically deforms the tube in the manner described above, and, if flow tube 10 is additionally excited into flexural vibrations, into a laterally acting excitation force. The excitation moment $M_{exc}$ may be bidirectional as shown schematically in FIG. 4 or 6, or unidirectional, and be adjusted in amplitude, for instance by means of a current- and/or voltage-regulator circuit, and in frequency, for instance by means of a phase-locked loop, in the manner familiar to those skilled in the art. From the electric excitation energy $E_{exc}$ necessary to maintain the torsional vibrations and the contingently additionally excited flexural vibrations of flow tube 10, the viscosity of the fluid can be derived in the manner familiar to those skilled in the art, cf. in particular U.S. Pat. Nos. 4,524,610, 5,253,533, 6,006,609, or EP-A 1 158 289.

Excitation assembly 40 may be, for example, a simple solenoid with a cylindrical excitation coil which is attached to flow tube 10 or antivibrator 20 and which in operation is traversed by a suitable excitation current, and with a permanent-magnet armature which is fixed to antivibrator 20 or flow tube 10 and rides, at least in part, in the excitation coil. Excitation assembly 40 may also be implemented with one or more electromagnets as shown in U.S. Pat. No. 4,524,610, for example.

To detect vibrations of flow tube 10, the transducer comprises a, particularly electrodynamic, sensor arrangement 50. This may be a sensor arrangement as is commonly used for such transducers, which senses the motions of flow tube 10, particularly on the inlet and outlet sides, by means of at least a first sensor 51, but contingently also by means of a second sensor 52, and converts them into corresponding sensor signals $S_1$, $S_2$ in the manner familiar to those skilled in the art. For the sensors 51, 52, electrodynamic velocity sensors, which measure the vibrations of flow tube 10 and antivibrator 20 relatively, or electrodynamic displacement or acceleration sensors may be used. Instead of electrodynamic sensor arrangements, sensor arrangements using resistive or piezoelectric strain gages or optoelectronic sensor arrangements may be employed. The sensor signals can be converted into the corresponding measured values by means of suitable, particularly digital, evaluation electronics in the manner familiar to those skilled in the art. Both the above-mentioned control electronics for excitation assembly 40 and the evaluation electronics connected to sensor arrangement 50 may be housed in an electronics case 200 which may be mounted on transducer case 100.

As shown in FIGS. 2 and 3, excitation assembly 40 is so designed and disposed in the transducer as to act on flow tube 10 and antivibrator 20 simultaneously, particularly differentially. Similarly, sensor arrangement 50 may be so designed and disposed in the transducer as to sense the vibrations of flow tube 10 and antivibrator 20 differentially.

In the above-described case where the torsional frequency and the flexural vibration frequency of the flow tube are chosen to be different, the transducer, based on a signal filtering process or a frequency analysis, for example, can separate the individual vibration modes both in the excitation signals and the sensor signals in a simple and advantageous manner even if torsional vibrations and flexural vibrations are excited simultaneously.

According to the invention, unlike the transducers of the above-mentioned U.S. Pat. No. 6,006,609 or EP-A 1 158 289, for example, the mass distributions of flow tube 10 and antivibrator 20 as well as of the sensor and excitation assemblies 50, 40 attached thereto are so adapted to one another that the internal transducer portion thus formed, which is mounted on the inlet and outlet tube sections 11, 12, has a centroid MS which is located at least within flow tube 10, but preferably as close as possible to the longitudinal axis L of the tube. In addition, the internal portion may preferably so designed that it has a first principal axis of inertia $T_1$ which is aligned with inlet tube section 11 and outlet tube section 12, and at least portions of which are located within flow tube 10. Because of the shifting of the centroid MS of the internal portion, but particularly because of the above-described location of the first principal axis of inertia $T_1$, the two forms of vibration of flow tube 10, namely the torsional vibrations and the flexural vibrations, which are largely balanced by antivibrator 20, are nearly perfectly isolated from each other. As a result, particularly unlike the transducers disclosed in U.S. Pat. Nos. 4,524,610, 5,253,533, or U.S. Pat. No. 6,006,609, both forms of vibration can now be readily excited separately in an advantageous manner.

The shifting of both the centroid MS and the first principal axis of inertia $T_1$ toward the longitudinal flow-tube axis L can be greatly simplified, for example, by designing the internal portion and arranging its constituents, i.e., flow tube 10, antivibrator 20, sensor arrangement 50, and excitation assembly 40, relative to each other in such a way that the mass distribution of the internal portion along the longitudinal flow-tube axis L is essentially symmetric, but at least invariant under an imaginary rotation about the longitudinal flow-tube axis L through 180° (c2 symmetry).

In a further embodiment of the invention, the preferably tubular and particularly largely axisymmetric antivibrator 20 is essentially coaxial with flow tube 10, whereby the attainment of a symmetric mass distribution of the internal portion is greatly simplified, so that the centroid MS is moved to a point close to the longitudinal flow-tube axis L in a simple manner.

In addition, sensor arrangement 50 and excitation assembly 40 are so designed and positioned relative to each other on flow tube 10 and antivibrator 20 that a moment of inertia developed by them is as concentric with the longitudinal flow-tube axis as possible or at least kept to a minimum. This can be achieved, for example, if a common centroid of sensor arrangement 50 and excitation assembly 40 is also located as close to the longitudinal flow-tube axis L as possible and/or if the total mass of sensor arrangement 50 and excitation assembly 40 is kept to a minimum.

In yet another embodiment of the invention, in order to excite torsional and/or flexural vibrations of flow tube 10 separately, excitation assembly 40 is so designed and so fixed to flow tube 10 and antivibrator 20 that a force producing the flexural vibrations will act on flow tube 10 along an imaginary line of force that runs outside a second principal axis of inertia $T_2$, an axis perpendicular to the first principal axis of inertia $T_1$, or intersects the second principal axis of inertia $T_2$ at one point at the most. In addition, the internal portion may be so designed that the second principal axis of inertia $T_2$ essentially coincides with the above-mentioned central axis.

Figure 4:
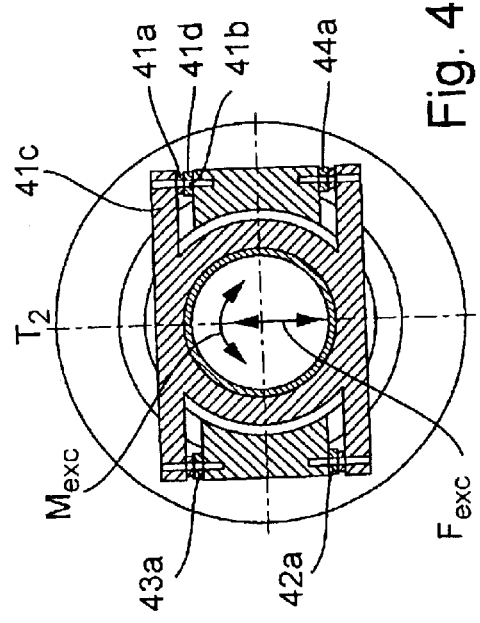
FIG. 4 is a first cross-sectional view of the transducer of FIG. 2.

In the embodiment shown in FIG. 4, excitation assembly 40 has a first excitation coil 41a, which in operation is at least intermittently traversed by the excitation current or a partial excitation current and which is fixed to a lever 41c connected to flow tube 10 and acts differentially on flow tube 10 and antivibrator 20 via this lever 41c and an armature 41b fixed to the outside of antivibrator 20. One of the advantages of this arrangement is that the cross section of antivibrator 20, and hence the cross section of transducer case 100, is kept small while excitation coil 41a is easily accessible, particularly during assembly. Another advantage of this embodiment of excitation assembly 40 is that any cup cores 41d used, which are not negligibly heavy, particularly with nominal diameters above 80 mm, can also be fixed to antivibrator 20 and thus have virtually no effect on the resonance frequencies of flow tube 10. At this point it should be noted, however, that, if necessary, it is also possible to fix excitation coil 41a to antivibrator 20, and armature 41b to flow tube 10.

In still another embodiment of the invention, particularly in order to meet the above-mentioned requirements placed on the mass distribution, excitation assembly 40 comprises at least a second excitation coil 42a, which is positioned along a diameter of flow tube 10 and which is coupled to flow tube 10 and antivibrator 20 in the same manner as excitation coil 41a. In yet another embodiment of the invention, the excitation assembly comprises two further excitation coils 43a, 44a, i.e., a total of four excitation coils arranged symmetrically at least with respect to the second principal axis of inertia $T_2$, which are all mounted in the transducer in the manner described above.

The force acting on flow tube 10 outside the second principal axis of inertia $T_2$ can be produced by means of such two- or four-coil arrangements in a simple manner if one of the excitation coils, e.g., excitation coil 41a, has an inductance different from the respective inductances of the others, or if in operation, one of the excitation coils, e.g., excitation coil 41a, is traversed by a partial excitation current different from the respective partial excitation currents through the other excitation coils.

Figure 5:
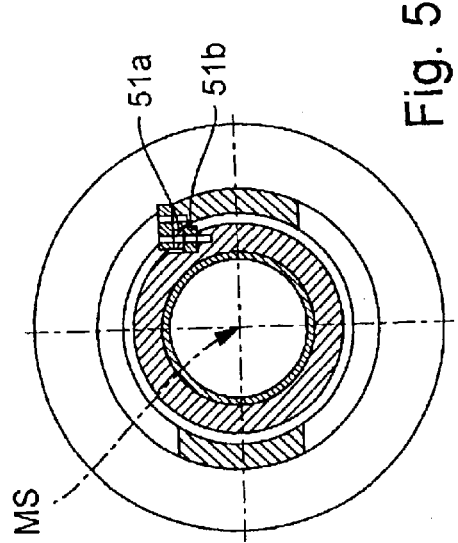
FIG. 5 is a second cross-sectional view of the transducer of FIG. 2.

In yet another embodiment of the invention, sensor arrangement 50, as shown schematically in FIG. 5, comprises a sensor coil 51a fixed to flow tube 10 outside the second principal axis of inertia $T_2$. Sensor coil 51a is located as close as possible to an armature 51b fixed to antivibrator 20 and is magnetically coupled to this armature in such a way that a variable measurement voltage which is influenced by rotational motions of and/or by lateral relative motions between flow tube 10 and antivibrator 20 is induced in the sensor coil. With sensor coil 51a positioned in accordance with the invention, both the above-mentioned torsional vibrations and the optionally excited flexural vibrations can be sensed simultaneously in an advantageous manner. If necessary, however, it is also possible to fix sensor coil 51a to antivibrator 20, and armature 51b, which is coupled to sensor coil 51a, to flow tube 10.

It should be noted that, if necessary, excitation assembly 40 and sensor arrangement 50 may also be virtually identical in mechanical design; furthermore, the aforementioned embodiments of the mechanical design of the excitation assembly 40 can also be applied for the most part to the mechanical design of sensor arrangement 40 and vice versa.

According to a development of the invention, grooves 201, 202 are provided in antivibrator 20 for adjusting the mass distribution of the internal portion. They make it possible to precisely set the torsional resonance frequencies of antivibrator 20, thus also providing improved isolation and/or permitting improved matching to the signal evaluation, cf. FIGS. 2 and 3. In addition, as also shown schematically in FIG. 3, the mass distribution of the internal portion can also be corrected by means of suitable counterbalance bodies 101, 102 fixed to flow tube 10. The counterbalance bodies 101, 102 may be, for example, metal rings slipped over, or metal platelets fixed to, flow tube 10.

As is readily apparent from the above explanations, the transducer according to the invention is characterized by a multitude of possible settings which enable those skilled in the art, particularly even after specification of external and internal mounting dimensions, to achieve high-quality balancing of torsional forces produced in flow tube 10 and in antivibrator 20, and hence to minimize the loss of torsional vibration energy to the environment of the transducer.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A vibratory transducer for a fluid flowing in a pipe, comprising:
    an essentially straight flow tube for conducting the fluid, said flow tube communicating with the connected pipe via an inlet tube section, ending in an inlet-side end of the flow tube, and an outlet tube section, ending in an outlet-side end of the flow tube, and said flow lube being at least intermittently vibrated in operation,
    an antivibrator fixed at the inlet-side end and the outlet-side end;
    an excitation assembly acting on the flow tube and the antivibrator for vibrating at least the flow tube; and
    a sensor arrangement for sensing vibrations of the flow tube,
    wherein in operation at least a portion of the flow tube performs torsional vibrations about an axis essentially aligned with the inlet lube section and the outlet tube section, particularly in order to produce shear forces in the fluid; and wherein an internal portion of the transducer, formed at least by the flow lube, the antivibrator, the sensor arrangement, and the excitation assembly and mounted at least on the inlet and outlet lube sections, has a centroid which is located within the flow tube.

2. A transducer as set forth in claim 1 wherein the centroid at the internal portion is located as precisely as possible an a longitudinal flow-tube axis, particularly on an axis aligned with the inlet tube section and the outlet tube section.

3. A transducer as set faith in claim 1 wherein the internal portion has a first principal axis of inertia which is essentially aligned with the inlet tube section and the outlet tube section and lies within the flow tube.

4. A transducer as sot forth in claim 1 wherein the internal portion has an essentially symmetric mass distribution with respect to the axis of torsional vibration.

5. A transducer as set forth in claim 1 wherein the antivibrator is essentially tubular in shape and essentially coaxial with the flow tube.

6. A transducer as set forth in claim 1 wherein a natural torsional frequency of the flow tube and a torsional natural frequency of the antivibrator are at least approximately equal.

7. A transducer as set forth in claim 1 wherein a torsional natural frequency of the antivibrator is greater than 0.8 times a torsional frequency of the flow tube.

8. A transducer as set forth in claim 1 wherein a torsional natural frequency of the antivibrator is less than 1.2 times a torsional frequency of the flow tube.

9. A transducer as set forth in claim 1 wherein the flow tube at least intermittently performs flexural vibrations about its longitudinal axis, particularly in order to induce Coriolis forces in the fluid.

10. A transducer as set forth in claim 9, wherein a frequency of torsional vibrations and a frequency of flexural vibrations of the flow tube are chosen to be different.

11. A transducer as sot forth in claim 1 wherein the excitation assembly is so designed and so fixed to the flow tube and the antivibrator that a force generating the flexural vibrations will act on the flow tube along an imaginary line of force which runs outside a second principal axis of inertia, an axis perpendicular to the first principal axis of inertia, or intersects the second principal axis of inertia at one point at the most.

12. A transducer as set forth in claim 1 wherein the excitation assembly comprises an excitation coil which is fixed to the flow tube, is at least intermittently traversed by an excitation current during operation, and acts on the flow tube and the antivibrator via a lever connected to the antivibrator and via an armature fixed in the lever.

13. A transducer as set forth in claim 1 wherein the sensor arrangement comprises a sensor coil disposed in the transducer outside the second principal axis of inertia as well as an armature magnetically coupled thereto whose relative position, particularly whose spacing, is changed as a result of torsional and, if excited, flexural vibrations of the flow tube and the antivibrator, whereby a variable measurement voltage is at least intermittently induced in the sensor coil.

14. A transducer as set forth in claim 1, said transducer comprising a transducer case fixed to the flow tube on the inlet and outlet tube sections.

15. A transducer as set forth in claim 1 wherein additional masses are fixed to the flow tube and/or grooves are formed in the antivibrator to adjust the mass distribution of the internal portion.

\* \* \* \* \*